(12) United States Patent
Kambara (10) Patent No.: US 10,842,383 B2
(45) Date of Patent: Nov. 24, 2020

(54) DENTAL HEALTH ASSESSMENT ASSISTING APPARATUS AND DENTAL HEALTH ASSESSMENT ASSISTING SYSTEM

(71) Applicant: Masaki Kambara, Osaka (JP)

(72) Inventor: Masaki Kambara, Osaka (JP)

(73) Assignee: Masaki Kambara, Osaka (JP)

( * ) Notice: Subject to any disclaimer, the term of this patent is extended or adjusted under 35 U.S.C. 154(b) by 65 days.

(21) Appl. No.: 16/099,824

(22) PCT Filed: May 10, 2017

(86) PCT No.: PCT/JP2017/017677
§ 371 (c)(1),
(2) Date: Nov. 8, 2018

(87) PCT Pub. No.: WO2017/195819
PCT Pub. Date: Nov. 16, 2017

(65) Prior Publication Data
US 2019/0110690 A1 Apr. 18, 2019

(30) Foreign Application Priority Data
May 10, 2016 (JP) ................................ 2016-094485

(51) Int. Cl.
*G06K 9/00* (2006.01)
*A61B 5/00* (2006.01)
(Continued)

(52) U.S. Cl.
CPC .............. *A61B 5/0088* (2013.01); *A61B 1/00* (2013.01); *A61B 1/04* (2013.01); *A61B 1/24* (2013.01);
(Continued)

(58) Field of Classification Search
USPC ........................................................ 382/128
See application file for complete search history.

(56) References Cited

U.S. PATENT DOCUMENTS

2007/0021670 A1 1/2007 Mandelis et al.
2010/0279248 A1 11/2010 Mourad et al.
(Continued)

FOREIGN PATENT DOCUMENTS

JP 2005069807 A 3/2005
JP 2009501579 A 1/2009
(Continued)

OTHER PUBLICATIONS

Extended Search Report for European Patent Application No. 17796179.4 dated Dec. 12, 2019.
(Continued)

*Primary Examiner* — Stephen P Coleman
(74) *Attorney, Agent, or Firm* — Masuvalley & Partners (57) ABSTRACT

The dental health assessment assisting apparatus includes a gray scale converter configured to convert a fluorescence image obtained by imaging fluorescence of a tooth irradiated with excitation light into a gray scale image, a gray scale value acquiring unit configured to acquire gray scale values of a reference point and a plurality of evaluation points in an image of the tooth in the gray scale image, a normalization unit configured to normalize the gray scale values of the plurality of evaluation points by the gray scale value of the reference point, and a dental health assessment data generator configured to generate dental health assessment data visually representing the gray scale value of the reference point and the gray scale values of the plurality of evaluation points which have been normalized.

6 Claims, 13 Drawing Sheets

(51) Int. Cl.
*A61B 1/24* (2006.01)
*A61C 19/04* (2006.01)
*A61B 1/00* (2006.01)
*A61B 1/04* (2006.01)
*G06K 9/42* (2006.01)
*G06K 9/46* (2006.01)

(52) U.S. Cl.
CPC ............ *A61B 5/0071* (2013.01); *A61B 5/742* (2013.01); *A61C 19/04* (2013.01); *G06K 9/42* (2013.01); *G06K 9/4661* (2013.01)

(56) References Cited

U.S. PATENT DOCUMENTS

| | | |
|---|---|---|
| 2010/0322490 A1 | 12/2010 | Pan et al. |
| 2011/0085713 A1 | 4/2011 | Yan et al. |
| 2011/0085715 A1* | 4/2011 | Yan .................... G06T 7/155 |
| | | 382/128 |
| 2012/0062716 A1* | 3/2012 | Dillon .................... A61C 9/006 |
| | | 348/66 |
| 2012/0261848 A1* | 10/2012 | Haraszati ........... A61C 13/0004 |
| | | 264/17 |
| 2014/0050376 A1 | 2/2014 | Yan et al. |

FOREIGN PATENT DOCUMENTS

| | | |
|---|---|---|
| JP | 2010-082210 A | 4/2010 |
| JP | 2011011055 A | 1/2011 |
| JP | 2011087929 A | 5/2011 |

OTHER PUBLICATIONS

PCT International Search Report in International Application No. PCT/US2017/017677 dated Jul. 25, 2017.
Korean Office Action dated May 29, 2020, issued in Korean Application No. 10-2018-7035701, total 9 pages.
Office Action of corresponding European patent application No. 17796179.4 dated Oct. 5, 2020.

* cited by examiner

FIG. 9A (A) FLUORESCENCE IMAGE

TRIMMING (B) TRIMMING IMAGE

EXTRACT CONTOUR

FIG. 9B (C) CONTOUR EXTRACTION IMAGE

AUTOMATICALLY SET REFERENCE POINT AND EVALUATION POINTS (D) EVALUATION POINT SET IMAGE

FIG. 10A

RELATIVE ANGLE OF EVALUATION POINT

FIG. 10B

DENTAL HEALTH ASSESSMENT ASSISTING APPARATUS AND DENTAL HEALTH ASSESSMENT ASSISTING SYSTEM

CROSS-REFERENCE TO RELATED PATENT APPLICATION

The present application is a National Stage Application of International Application No. PCT/JP2017/017677 entitled "DENTAL HEALTH ASSESSMENT ASSISTING APPARATUS AND DENTAL HEALTH ASSESSMENT ASSISTING SYSTEM" filed May 10, 2017, which claims priority to Japanese Patent Application Number 2016-094485 filed May 10, 2016, each of which is incorporated herein by reference in their entirety.

TECHNICAL FIELD

The present invention relates to a dental health assessment assisting apparatus and a dental health assessment assisting system which assist dentists to assess dental health.

BACKGROUND ART

An example of preventive dentistry is a diagnosis of early caries. Caries has been diagnosed by ocular inspection and/or by using a CPI probe. In recent years, a Quantitative Light-induced Fluorescence (QLF) method of non-invasively, objectively and quantitatively evaluating early caries has been used (for example, see Patent Literature 1). The QLF method is a diagnosis method based on emission of fluorescence of a tooth when the tooth is irradiated with blue-violet light (excitation light).

CITATION LIST

Patent literature

Patent Literature 1: JP 2011-11055 A

SUMMARY OF INVENTION

Technical Problem

If it is possible to assess dental health, namely whether a tooth is a weak tooth in which caries easily develops or a strong tooth in which the caries hardly develops, more effective preventive dentistry can be provided. For example, if it is determined that the tooth is a weak tooth, health guidance and/or preventive care can be provided to create an oral environment in which caries is less likely to develop. However, known preventive dentistry such as the QLF method can diagnose early caries, but assessment of dental health by the known preventive dentistry is difficult.

In view of the foregoing, it is an object of the present invention to provide a dental health assessment assisting apparatus and a dental health assessment assisting system which assist dentists to assess dental health.

Solution to Problem

A dental health assessment assisting apparatus according to an aspect of the present invention includes a gray scale converter configured to convert a fluorescence image obtained by imaging fluorescence of a tooth irradiated with excitation light into a gray scale image, a gray scale value acquiring unit configured to acquire gray scale values of a reference point and a plurality of evaluation points in an image of the tooth in the gray scale image, and a dental health assessment data generator configured to generate dental health assessment data visually representing the gray scale value of the reference point and the gray scale values of the plurality of evaluation points.

The dental health assessment assisting apparatus may further include a normalization unit configured to normalize the gray scale values of the plurality of evaluation points by the gray scale value of the reference point, wherein the dental health assessment data generator may be configured to visually represent the gray scale values of the plurality of evaluation points normalized by the normalization unit in the dental health assessment data.

The normalization unit may be configured to normalize the gray scale values of the plurality of evaluation points by dividing the gray scale values of the plurality of evaluation points by the gray scale value of the reference point.

The dental health assessment data generator may be configured to generate a graph representing aging of the gray scale value of the reference point and the gray scale values of the plurality of evaluation points as the dental health assessment data.

For example, the reference point is a point at a maximum elevated portion of a tooth, and the evaluation points are points at a marginal portion of the tooth (a tooth enamel portion).

The gray scale value acquiring unit may be configured to extract an entire image of the tooth from the gray scale image to obtain the center of gravity or the center of the entire image of the tooth, to set, as the reference point, a point having a maximal luminance in the entire image of the tooth, and to set, as the plurality of evaluation points, points located on a plurality of virtual lines with a predetermined distance from an edge of the tooth in a direction to the center of gravity or the center, the virtual lines passing the center of gravity or the center and forming a predetermined angle with respect to a 0-degree axis connecting the center of gravity or the center to the reference point.

The dental health assessment assisting system according to the present invention includes the dental health assessment assisting apparatus, an imaging apparatus configured to generate a fluorescence image by irradiating a tooth with excitation light to image fluorescence of the tooth, and a display apparatus configured to display the dental health assessment data generated by the dental health assessment assisting apparatus.

Advantageous Effects of Invention

According to the present invention, dental health assessment data is generated by analyzing a fluorescence image obtained by imaging fluorescence of a tooth irradiated with excitation light, and a dentist can assess dental health with reference to the dental health assessment data.

DESCRIPTION OF EMBODIMENTS

With reference to the drawings as necessary, embodiments will be described in detail below. Note that unnecessarily detailed description may be omitted. For example, detailed description of already well-known matters and repeated description of substantially the same configurations may be omitted. This is to avoid that the following description becomes unnecessarily redundant and to facilitate understanding of the following description by those skilled in the art.

Note that the inventor provides the attached drawings and the following description for a full understanding of the present invention by those skilled in the art, but the inventor does not intend to limit the subject-matter in the claim by attached drawings and the following description.

Figure 1:
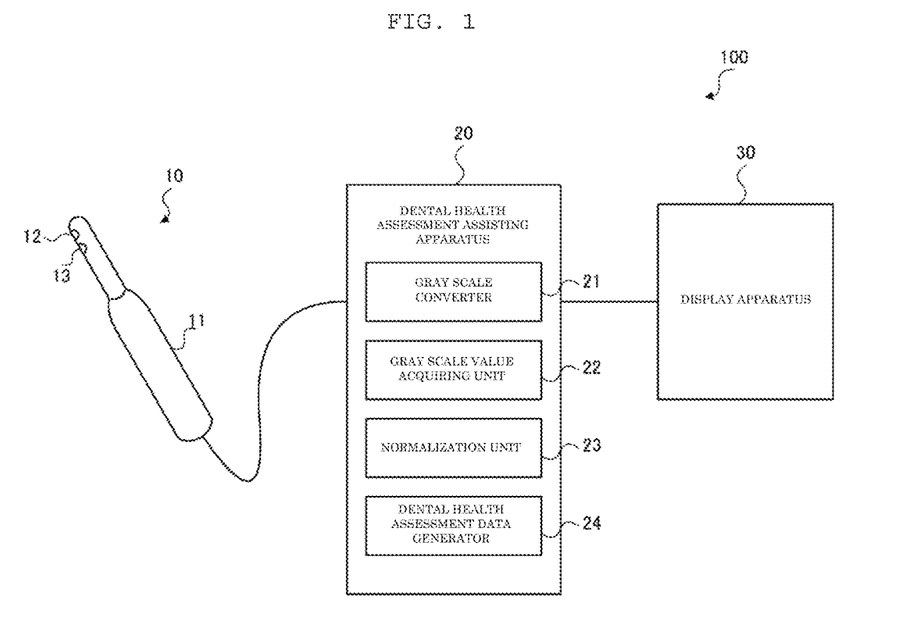
FIG. 1 is a view illustrating a configuration of a dental health assessment assisting system according to one embodiment of the present invention.

FIG. 1 is a view illustrating a configuration of a dental health assessment assisting system according to one embodiment of the present invention. A dental health assessment assisting system 100 according to the present embodiment includes an imaging apparatus 10, a dental health assessment assisting apparatus 20, and a display apparatus 30.

The imaging apparatus 10 is an apparatus configured to irradiate a tooth with excitation light to image fluorescence of the tooth. Specifically, the imaging apparatus 10 includes a body 11, a light source 12, and a camera 13.

The body 11 is a hollow rod-like member. In the hollow of the body 11, various types of electronic substrates are disposed. The body 11 has a tip portion at which the light source 12 and the camera 13 are disposed in proximity to each other. The tip portion of the body 11 is configured to be inserted into the oral cavity of a patient.

The light source 12 is a device configured to emit blue-violet light (excitation light) having a specified wavelength (370±40 nm). For example, the light source 12 may be configured by combining a filter which transmits light having the specified wavelength with a Light Emitting Diode (LED) or a xenon lamp.

The camera 13 is a device configured to perform photo-electric conversion of light from an object to generate image data. For example, the camera 13 may include an optical system and a Charge Coupled Device (CCD) image sensor. Note that the optical system may include a filter which transmits only green to yellow-green light.

In the dental health assessment assisting system 100, the imaging apparatus 10 is used to acquire a fluorescence image of a tooth. Enamel on an outermost surface layer of a tooth crown has a property of transmitting light similarly to glass. Moreover, a boundary portion between the enamel and dentin as an inner layer of the enamel has a property of emitting fluorescence when irradiated with light having the specified wavelength. In particular, a fluorescent material between the enamel and the dentin is excited to emit intense fluorescence when irradiated with the excitation light having the specified wavelength, and the fluorescence is emitted outside through the enamel. The imaging apparatus 10 images such fluorescence of a tooth.

Figure 2:
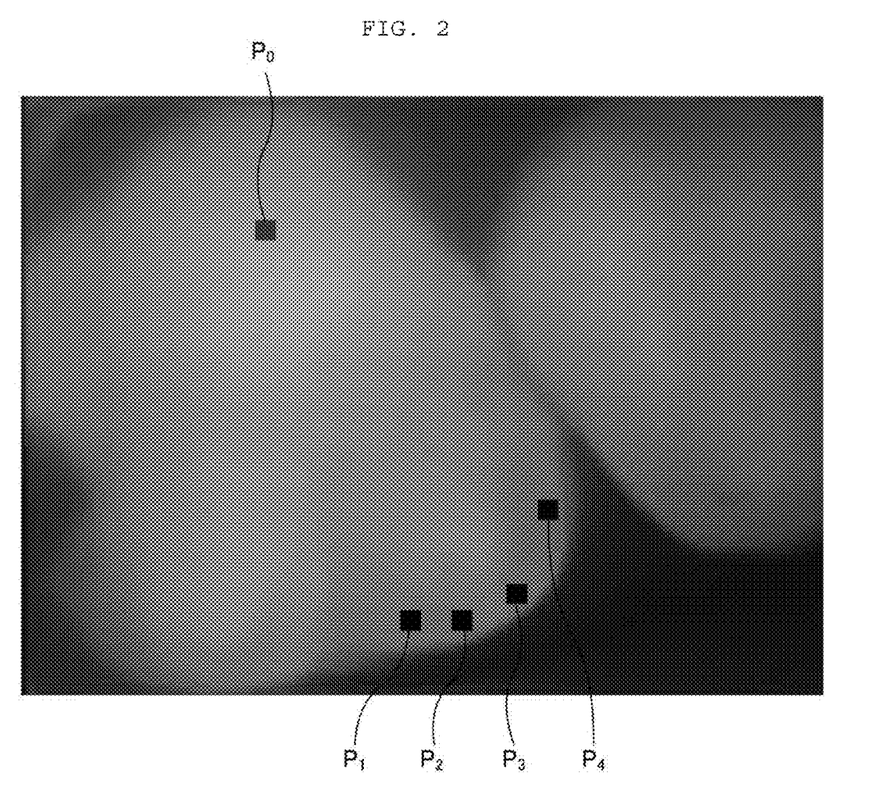
FIG. 2 is a fluorescent image of a tooth according to an example.

FIG. 2 shows an example of a fluorescence image of a tooth imaged by the imaging apparatus 10. The image is obtained by imaging an occlusion surface of an upper right first molar tooth. Note that an image of the tooth in the actual image is in green to yellow-green color, but for the sake of description, the image is shown in gray scale in FIG. 2.

Referring back to FIG. 1, the dental health assessment assisting apparatus 20 is an apparatus configured to receive the fluorescence image of the tooth from the imaging apparatus 10 and to process the fluorescence image, thereby generating dental health assessment data which helps dentists assess dental health. The imaging apparatus 10 and the dental health assessment assisting apparatus 20 are cable-connected to each other by a Universal Serial Bus (USB) cable, a network cable, or the like. Alternatively, the imaging apparatus 10 and the dental health assessment assisting apparatus 20 may be wirelessly connected to each other via WiFi (registered trademark), Bluetooth (registered trademark), or the like.

The dental health assessment assisting apparatus 20 may include a Personal Computer (PC), a mainframe computer such as a server apparatus, or the like. The dental health assessment assisting apparatus 20 may be realized as Software as a Service (Saas) on the cloud. In this case, the imaging apparatus 10, the dental health assessment assisting apparatus 20, and the display apparatus 30 are connected to one another via a network such as the Internet.

Specifically, the dental health assessment assisting apparatus 20 includes a gray scale converter 21, a gray scale value acquiring unit 22, a normalization unit 23, and a dental health assessment data generator 24. Note that the gray scale converter 21, the gray scale value acquiring unit 22, the normalization unit 23, and the dental health assessment data generator 24 may include software, hardware, or a combination thereof.

The gray scale converter 21 converts the fluorescence image obtained by imaging fluorescence of the tooth irradiated with the excitation light into a gray scale image. The fluorescence image of the tooth is, for example, an RGB color image. As described above, the fluorescence image includes an image of the tooth in green to yellow-green color. The gray scale converter 21 converts the fluorescence image of the tooth into a HSV color space and then deletes hue information (Hue) and saturation information (Saturation) with luminance information (Value) being maintained, so that a gray scale image can be obtained. Note that the gray scale image may have any number of gradations and has, for example, 256 gradations.

The gray scale value acquiring unit 22 acquires gray scale values of a reference point and a plurality of evaluation points in an image of the tooth in the gray scale image after the conversion by the gray scale converter 21. For example, in the fluorescence image of the tooth in FIG. 2, a point P0 is a reference point, and points P1, P2, P3, and P4 are evaluation points. Note that in a gray scale image having 256 gradations, the gray scale value at the darkest point is "255", and the gray scale value at the whitest point is "0". That is, in the gray scale image, the darker, the larger the gray scale value is.

Figure 3:
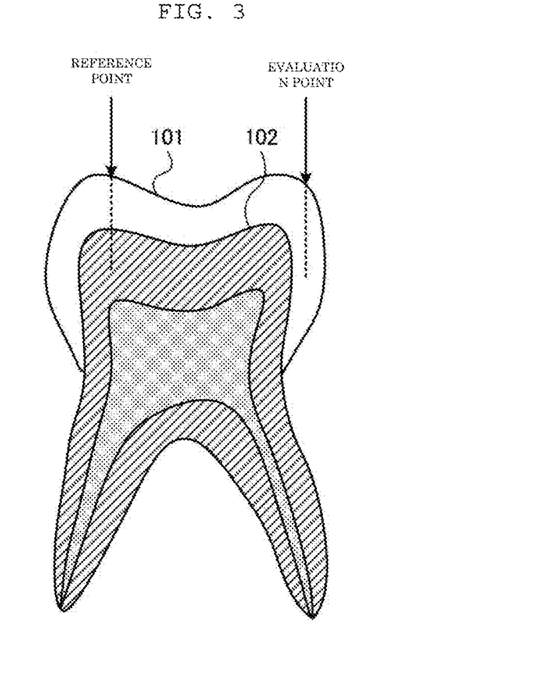
FIG. 3 is a longitudinal section of a tooth according to an example.

FIG. 3 is a longitudinal section of a tooth (a molar tooth). With reference to the longitudinal section, the reference point and the evaluation points will be described. The reference point is set at a position at which fluorescence at an interface between enamel 101 and dentin 102 can be captured.

Here, the fluorescence at the interface between the enamel 101 and the dentin 102 is transmitted through the enamel 101 and arrives at a surface layer, but if decalcification of the enamel 101 has advanced due to early caries or the like, the crystallinity of the enamel 101 deteriorates, and light is irregularly reflected, and consequently, the fluorescence at the interface between the enamel 101 and the dentin 102 in the surface layer of the tooth cannot be correctly captured. Thus, a point at the maximum elevated portion which is less likely to suffer from the early caries and in which the crystallinity of the enamel 101 is relatively stable is preferably set as the reference point. Thus, at the evaluation points, fluorescence transmitted through the enamel 101 in a column direction of an enamel prism can be captured.

The evaluation points are set at positions at which only fluorescence of the enamel 101 can be captured. For example, points at a marginal portion of a tooth may be determined as the evaluation points. At the evaluation points, fluorescence transmitted across the column of the enamel prism is captured. Thus, if the crystallinity of the enamel 101 deteriorates, light is irregularly reflected, and fluorescence of the enamel 101 captured at the evaluation points is bright. In contrast, if the crystallinity of the enamel 101 is good, light is less likely to be irregularly reflected, and fluorescence of the enamel 101 captured at the evaluation points is dark. Thus, the quality of the crystallinity of the enamel 101 can be determined on the basis of the brightness and the darkness at the evaluation points in the gray scale image.

Figure 7A:
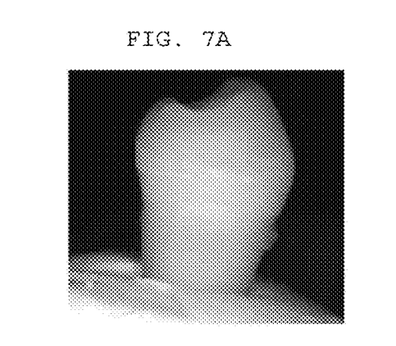
FIG. 7A is a visible light photographic image of a healthy tooth.
Figure 7B:
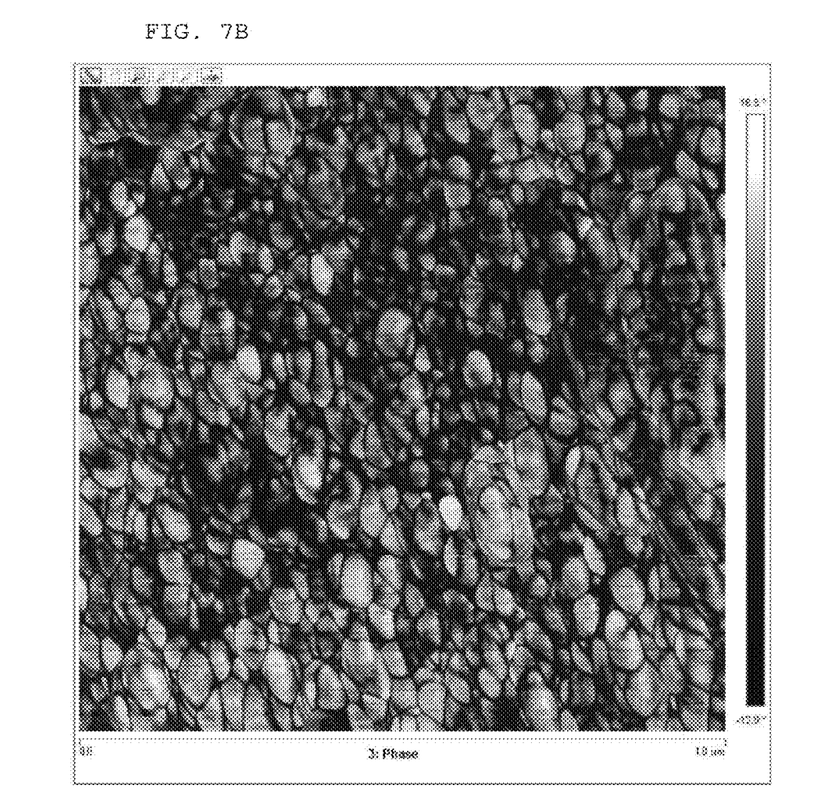
FIG. 7B is an atomic force microscope image (1 μm visual field) of a surface of a healthy tooth.
Figure 7C:
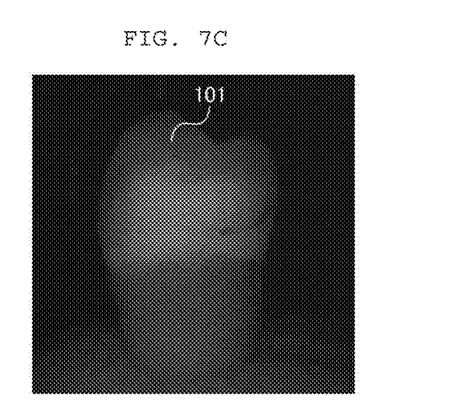
FIG. 7C is a fluorescence image of a healthy tooth.

FIG. 7A shows a visible light photographic image of a healthy tooth. FIG. 7B shows an atomic force microscope image (1 μm visual field) of a surface of a healthy tooth. FIG. 7C shows a fluorescence image of a healthy tooth. As can be seen from FIGS. 7B and 7C, in the healthy tooth, enamel particles have a substantially uniform shape (see FIG. 7B), and the enamel 101 becomes less likely to irregularly reflect light and is thus dark in the fluorescence image (see FIG. 7C).

Figure 8A:
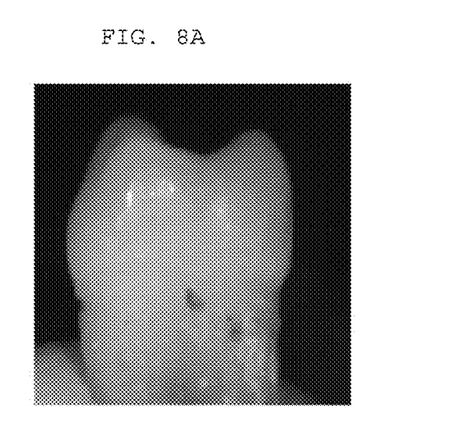
FIG. 8A is a visible light photographic image of an unhealthy tooth.
Figure 8B:
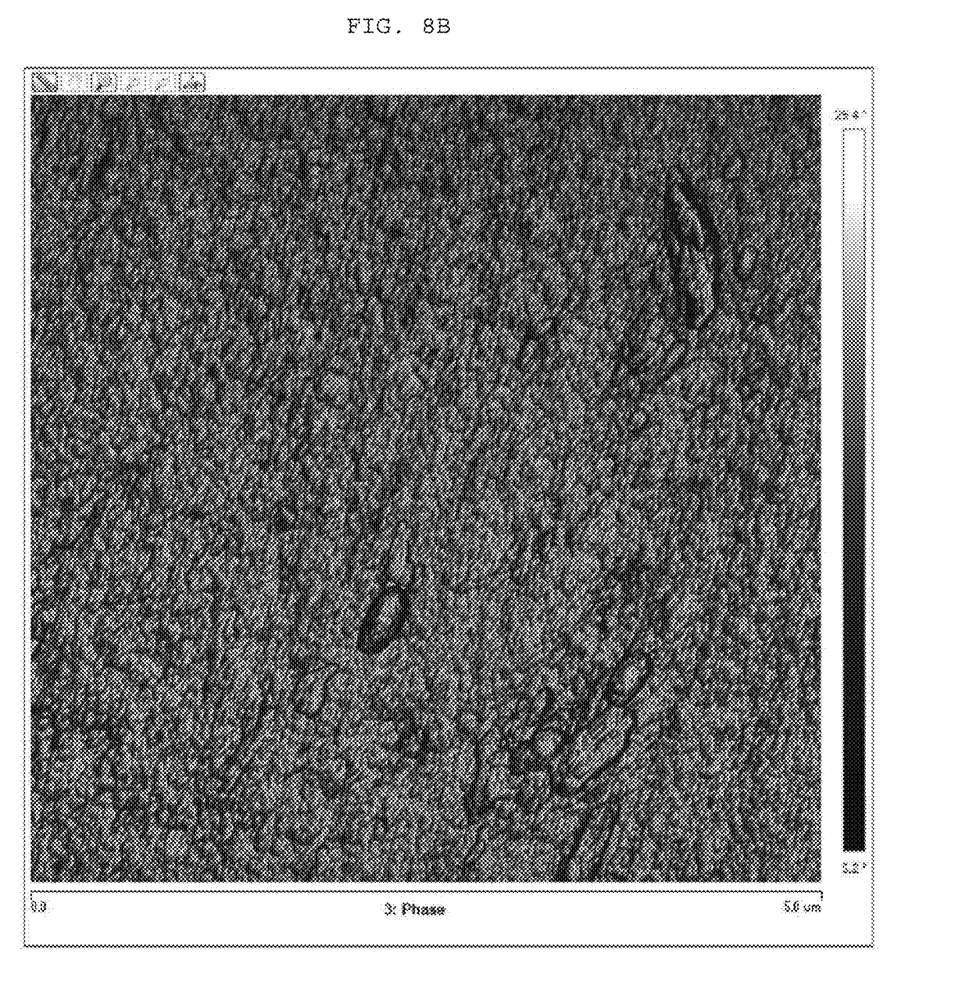
FIG. 8B is an atomic force microscope image (5 μm visual field) of a surface of an unhealthy tooth.
Figure 8C:
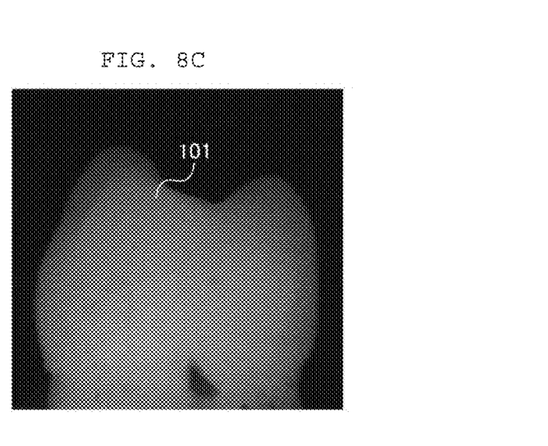
FIG. 8C is a fluorescence image of an unhealthy tooth.

FIG. 8A shows a visible light photographic image of an unhealthy tooth. FIG. 8B shows an atomic force microscope image (5 μm visual field) of a surface of an unhealthy tooth. FIG. 8C shows a fluorescence image of an unhealthy tooth. As can be seen from FIGS. 8B and 8C, in the unhealthy tooth, irregularity of enamel particles is observed in a plurality of locations (see FIG. 8B), and the enamel 101 irregularly reflects light and is thus bright in the fluorescence image (see FIG. 8C).

Referring back to FIG. 1, the normalization unit 23 normalizes the gray scale values of the plurality of evaluation points by the gray scale value of the reference point in the gray scale image. For example, the normalization unit 23 normalizes the gray scale values of the plurality of evaluation points by dividing the gray scale values of the plurality of evaluation points by the gray scale value of the reference value. In this case, if the evaluation points are darker than the reference point in the gray scale image, the normalization value of each evaluation point is larger than 1. However, if the reference point is substantially as bright as the evaluation points, the normalization value of each evaluation point is substantially 1.

Thus, normalizing the gray scale values of the evaluation points enables a plurality of gray scale images to be compared with each other in terms of the magnitude relationship of the gray scale values of the evaluation points without being influenced by an effect that the gray scale image becomes overall bright or dark due to individual difference and/or differences in imaging condition even when such an effect occurs.

Note that other than the above-described example, for example, a difference between the gray scale value of the reference point and the gray scale value of each evaluation point may be set as the normalization value.

The dental health assessment data generator 24 generates dental health assessment data visually representing the gray scale value of the reference point and the gray scale values of the plurality of evaluation points in a gray scale image. For example, to a fluorescence image of a tooth imaged by the imaging apparatus 10 or a gray scale image obtained by conversion by the gray scale converter 21, gray scale values of a reference point and a plurality of evaluation points may be added to obtain the dental health assessment data. Alternatively, to a fluorescence image of a tooth or a gray scale image thereof, gray scale values of a plurality of evaluation points normalized by the normalization unit 23, that is, normalization values may be added to obtain the dental health assessment data.

Moreover, by storing fluorescence images or gray scale images thereof, the dental health assessment data generator 24 can generate a graph representing aging of the gray scale value of the reference point and the gray scale values of the plurality of evaluation points as the dental health assessment data.

The display apparatus 30 is a display apparatus configured to display the dental health assessment data generated by the dental health assessment assisting apparatus 20. A dentist watches the dental health assessment data displayed on the display apparatus 30, which enables the dentist to assess the dental health.

Next, with reference to fluorescence images of teeth of elementary school children obtained in regular dental check-ups, an example use of the dental health assessment assisting system 100 will be described.

Figure 4A:
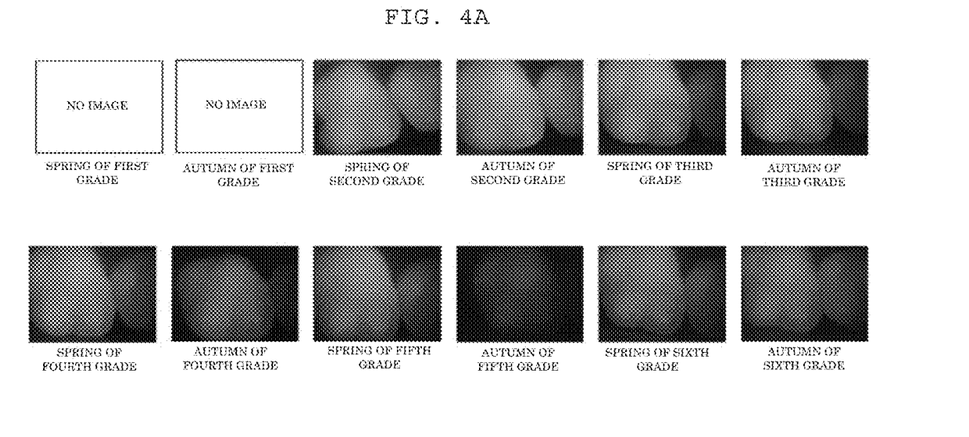
FIG. 4A shows fluorescence images of a schoolchild's tooth imaged in regular dental checkups.

FIG. 4A shows fluorescence images of a tooth of a schoolchild imaged in regular dental checkups. Each fluorescence image in FIG. 4A is an image of an occlusion surface of an upper right first molar tooth of the schoolchild. Caries did not develop in the tooth of this schoolchild for six years. That is, FIG. 4A shows an example of fluorescence images of a "strong tooth". Note that the regular dental checkups are done in spring and autumn every year, but fluorescence images of the tooth of this schoolchild were not obtained in the regular dental checkups in spring and autumn of the first grade.

Figure 4B:
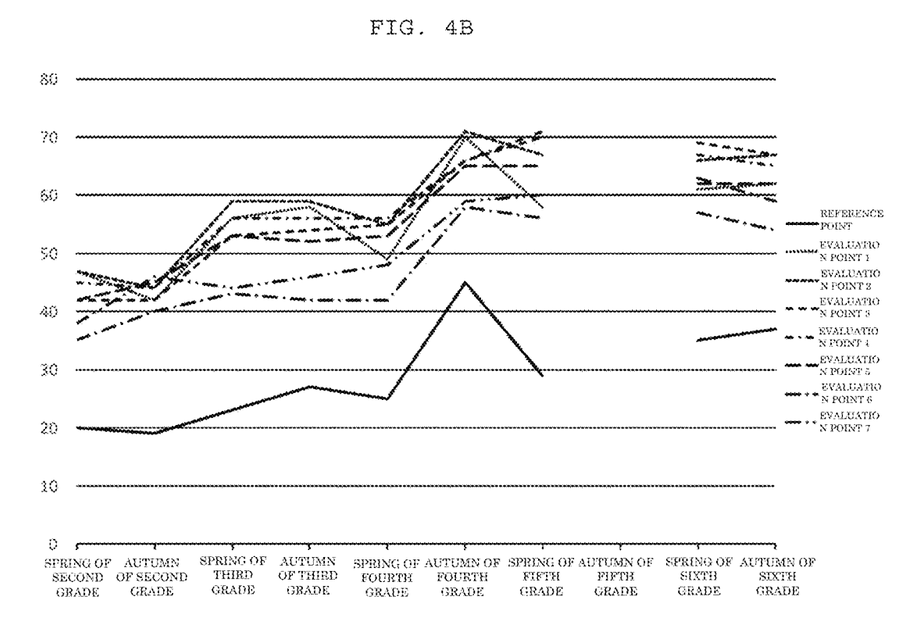
FIG. 4B is a graph illustrating aging of each of gray scale values of a reference point and seven evaluation points obtained by analyzing the fluorescence images of FIG. 4A.

The graph of FIG. 4B shows aging of gray scale values of a reference point and seven evaluation points obtained by analyzing the fluorescence images in FIG. 4A. In each fluorescence image in FIG. 4A, a point at a maximum elevated portion is set as the reference point, and seven points at a marginal portion are set as the evaluation points. The graph is displayed by the display apparatus 30. Note that since the fluorescence image in autumn of the fifth grade was generally dark and unclear, it was not possible to set the reference point and the evaluation points, and the gray scale values of the reference point and the evaluation points in autumn of the fifth grade were not obtained.

As can be seen from the graph of FIG. 4B, in the strong tooth, the gray scale value of the reference point remains smaller than the gray scale value of each evaluation point. Moreover, in the strong tooth, a tendency is observed that the gray scale values of all the reference point and the evaluation points increase as time passes (all the points are imaged darkly in the gray scale image).

Figure 4C:
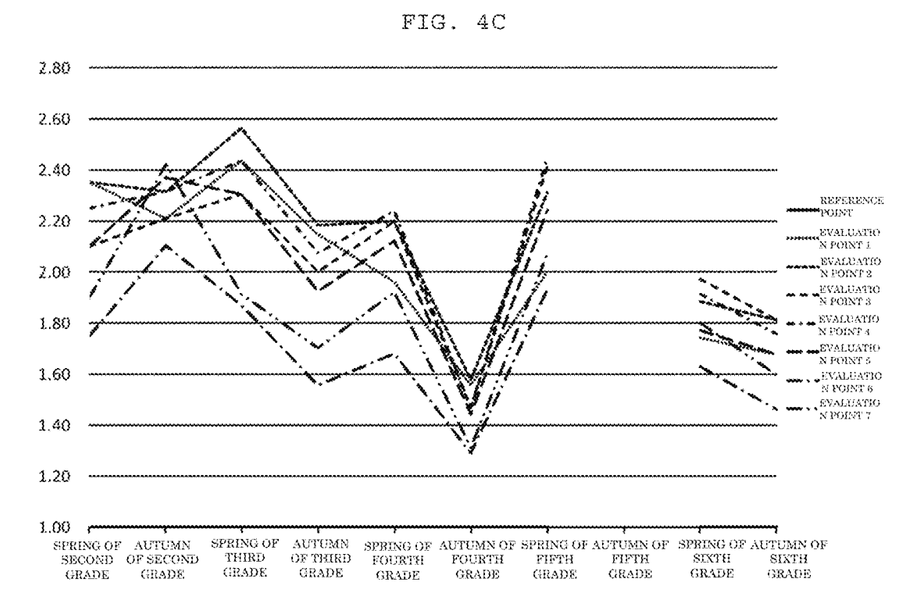
FIG. 4C is a graph in which the gray scale values of FIG. 4B are normalized.

The graph of FIG. 4C shows the gray scale values in FIG. 4B after the normalization. The graph is displayed by the display apparatus 30. As can be seen from this graph, in the strong tooth, the normalization value of each evaluation point is larger than or equal to about 1.5 and is often larger than or equal to 2.

Figure 5A:
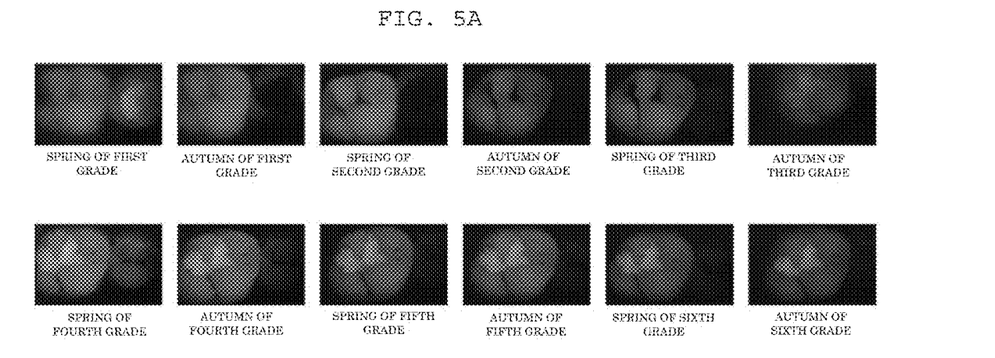
FIG. 5A shows fluorescence images of another schoolchild's tooth imaged in regular dental checkups.

FIG. 5A shows a fluorescence image of another schoolchild's tooth imaged in regular dental checkups. Each fluorescence image of FIG. 5A is an image of an occlusion surface of an upper right first molar tooth of the schoolchild. It can be seen that caries developed in the tooth of the schoolchild, and a filling of the caries was observed in the regular dental checkup in autumn of the third grade. That is, FIG. 5A shows an example of fluorescence images of a "weak tooth".

Figure 5B:
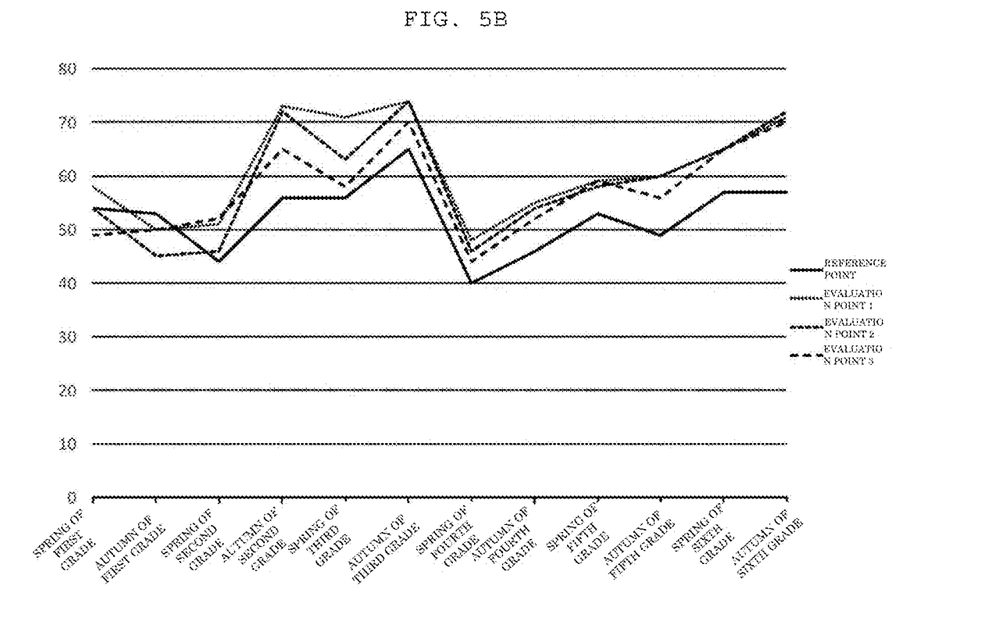
FIG. 5B is a graph illustrating aging of each of gray scale values of a reference point and three evaluation pints obtained by analyzing the fluorescence images of FIG. 5A.

The graph of FIG. 5B shows aging of gray scale values of a reference point and three evaluation points obtained by analyzing the fluorescence images of FIG. 5A. In each fluorescence image in FIG. 5A, a point at a maximum elevated portion is set as the reference point, and three points at a marginal portion are set as the evaluation points. The graph is displayed by the display apparatus 30.

As can be seen from the graph of FIG. 5B, in the weak tooth, the gray scale value of the reference point is almost equal to the gray scale value of each evaluation point. Moreover, in the weak tooth, the gray scale values of all the reference point and the evaluation points change as time passes, but a tendency that the gray scale values of all the reference point and the evaluation points increase as time passes (all the points are imaged darkly in the gray scale image) is not observed.

Figure 5C:
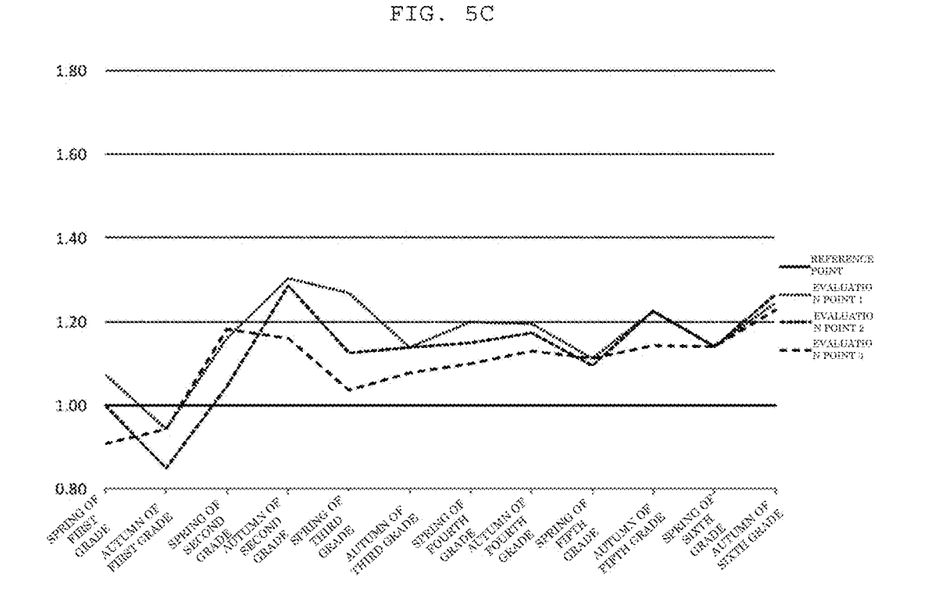
FIG. 5C is a graph in which the gray scale values of FIG. 5B are normalized.

The graph of FIG. 5C shows the gray scale values of FIG. 5B after the normalization. The graph is displayed by the display apparatus 30. As can be seen from this graph, in the weak tooth, the normalization value of each evaluation point is smaller than or equal to about 1.2 and may be smaller than or equal to 1.

Figure 6A:
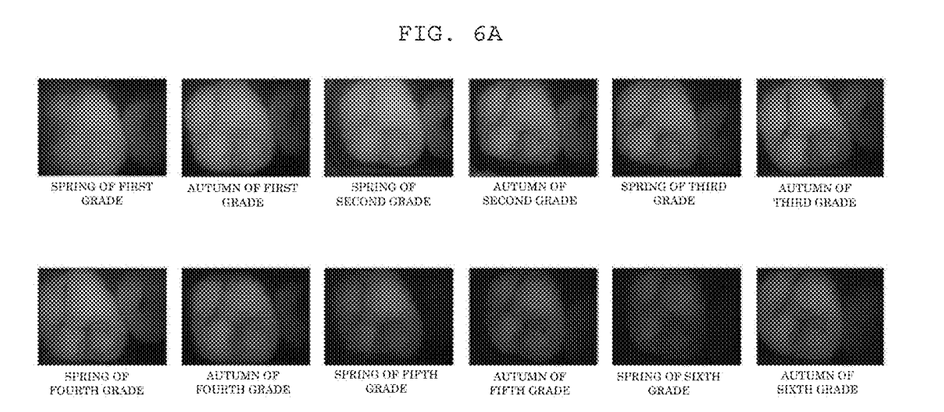
FIG. 6A shows fluorescence images of still another schoolchild's tooth imaged in regular dental checkups.

FIG. 6A shows a fluorescence image of still another schoolchild's tooth imaged in regular dental checkups. Each fluorescence image of FIG. 6A is an image of an occlusion surface of an upper right first molar tooth of the schoolchild. An early caries was observed in the tooth of this schoolchild. That is, FIG. 6A shows an example of fluorescence images of a "weak tooth".

Figure 6B:
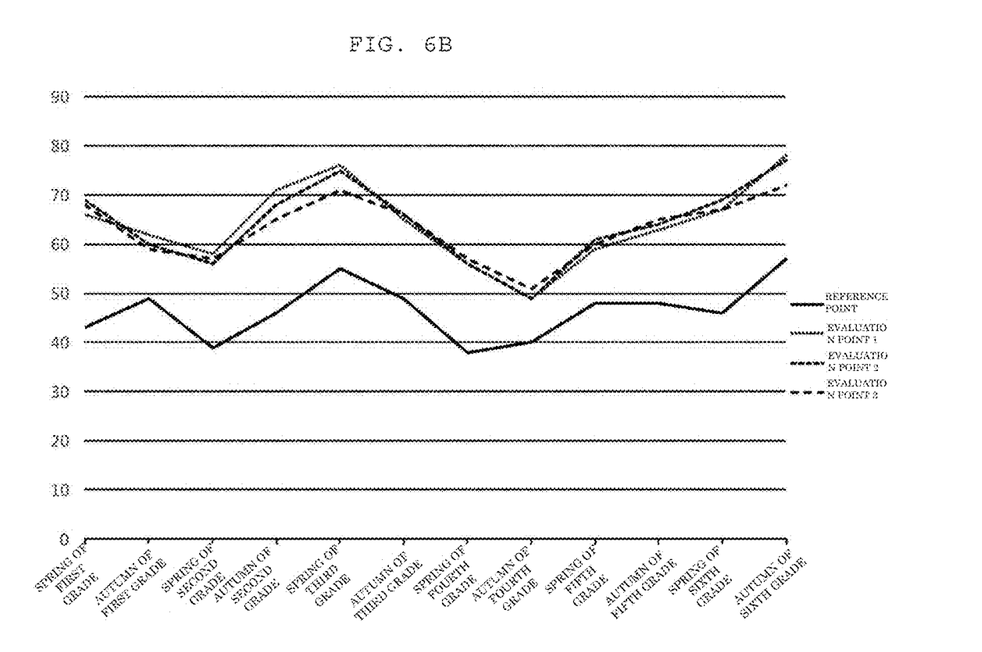
FIG. 6B is a graph illustrating aging of each of gray scale values of a reference point and three evaluation pints obtained by analyzing the fluorescence images of FIG. 6A.

The graph of FIG. 6B shows aging of gray scale values of a reference point and three evaluation points obtained by analyzing the fluorescence images of FIG. 6A. In each fluorescence image in FIG. 6A, a point at a maximum elevated portion is set as the reference point, and three points at a marginal portion are set as the evaluation points. The graph is displayed by the display apparatus 30. As can be seen from this graph, in the weak tooth, the gray scale values of all the reference point and the evaluation points change as time passes, but a tendency that the gray scale values of all the reference point and the evaluation points increase as time passes (all the points are imaged darkly in the gray scale image) is not observed.

Figure 6C:
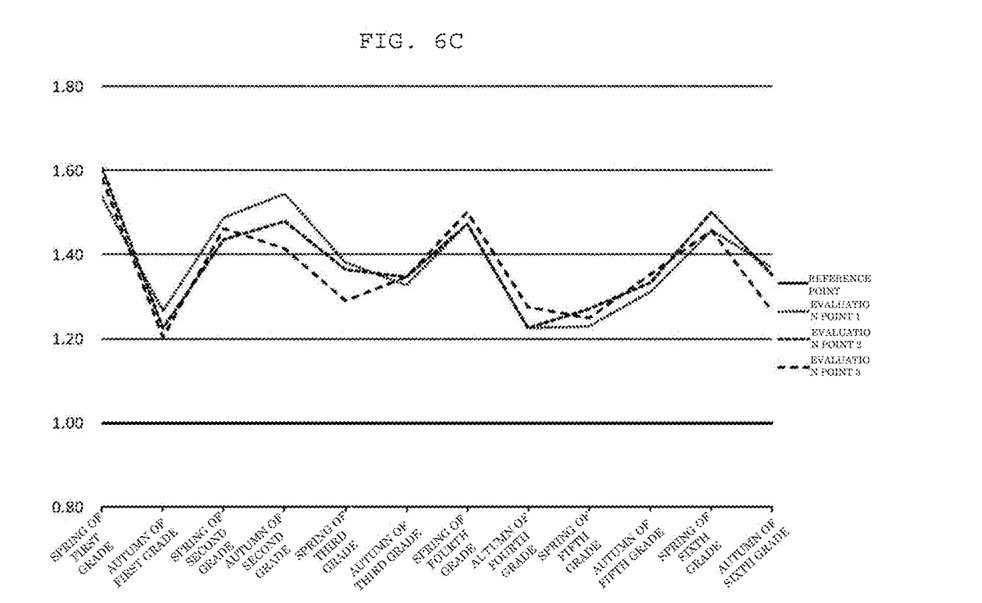
FIG. 6C is a graph in which the gray scale values of FIG. 6B are normalized.

The graph of FIG. 6C shows the gray scale values of FIG. 6B after the normalization. The graph is displayed by the display apparatus 30. As can be seen from this graph, in the weak tooth, the normalization value of each evaluation point is about 1.4.

Figure 9A:
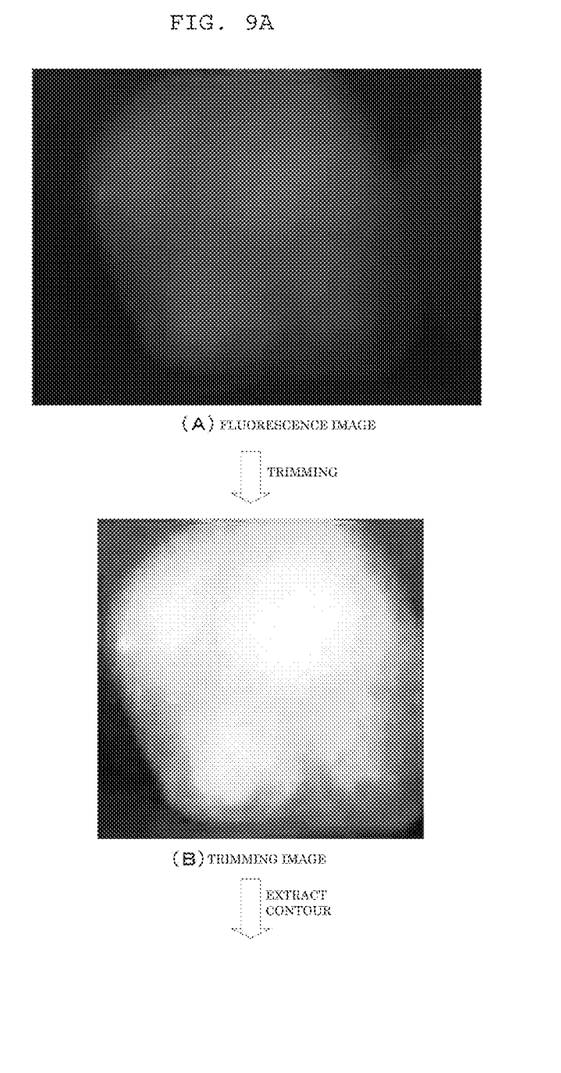
FIG. 9A is a view illustrating a sequence of processes of a gray scale image obtained by imaging a tooth.
Figure 9B:
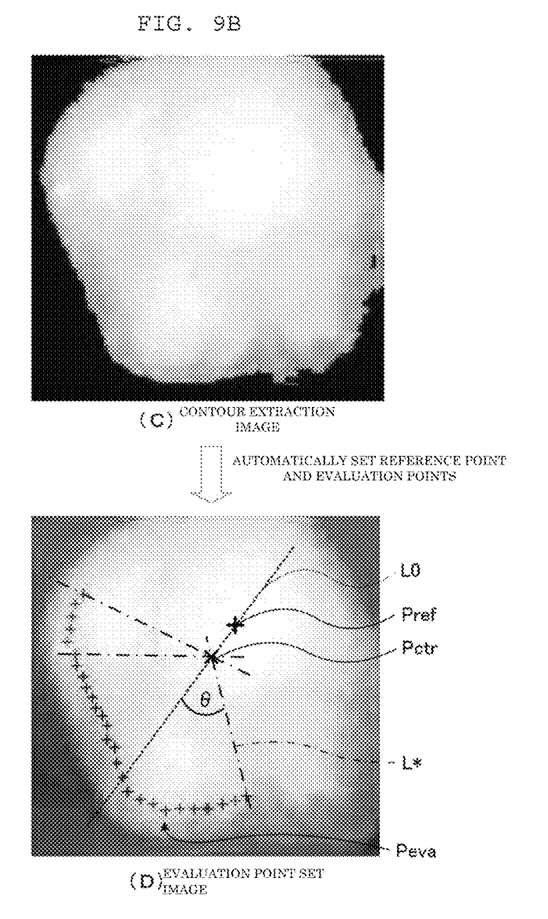
FIG. 9B is a view illustrating a sequence of processes which follows the sequence in FIG. 9A.

Note that the reference point and the evaluation points can be automatically set by the gray scale value acquiring unit 22 in, for example, a manner described below. FIGS. 9A and 9B show a sequence of processes of a gray scale image obtained by imaging a tooth.

The gray scale value acquiring unit 22 trims away an unnecessary part around the tooth in a fluorescence image obtained by imaging fluorescence of a tooth irradiated with excitation light, converts the fluorescence image into a gray scale image, and further extracts a contour of the tooth, that is, an entire image of the tooth from the gray scale image. The gray scale value acquiring unit 22 obtains the center of gravity or the center Pctr of an entire image of the tooth and sets a point having a maximal luminance in the entire image of the tooth as a reference point Pref.

When the center of gravity or the center Pctr and the reference point Pref are determined, the gray scale value acquiring unit 22 sets a 0-degree axis L0 connecting the center of gravity or the center Pctr to the reference point Pref and sets a plurality of virtual lines L* passing through the center of gravity or the center Pctr and forming a predetermined angle θ with respect to the 0-degree axis L0. Note that the predetermined angle θ can be set in units of, for example, 5° within a relative angle given to the 0-degree axis L0. The range of the relative angle and the predetermined angle θ can be arbitrarily set by a user. When the plurality of virtual lines L* are set, the gray scale value acquiring unit 22 sets, as a plurality of evaluation points Peva, points located on the virtual lines L* with a predetermined distance from an edge of the tooth in a direction to the center of gravity or the center Pctr. In this way, the reference point and the evaluation points are automatically set.

Figure 10A:
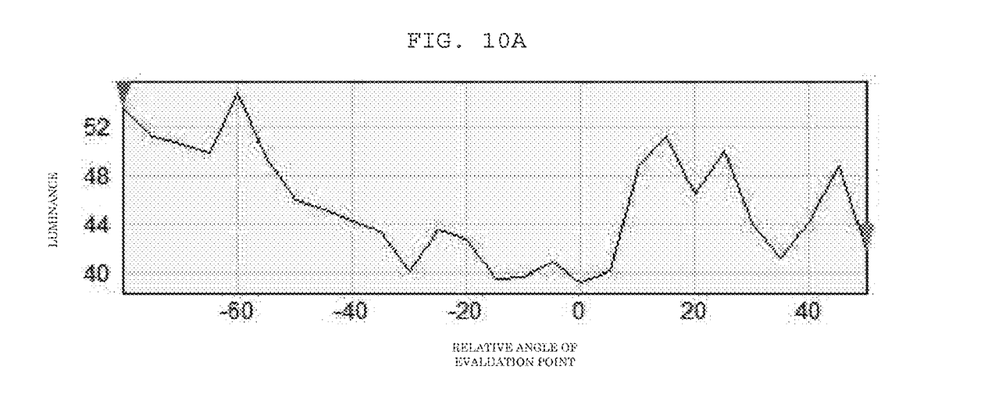
FIG. 10A is a graph illustrating the luminance of each of evaluation points in the image of the tooth illustrated in FIG. 9B.
Figure 10B:
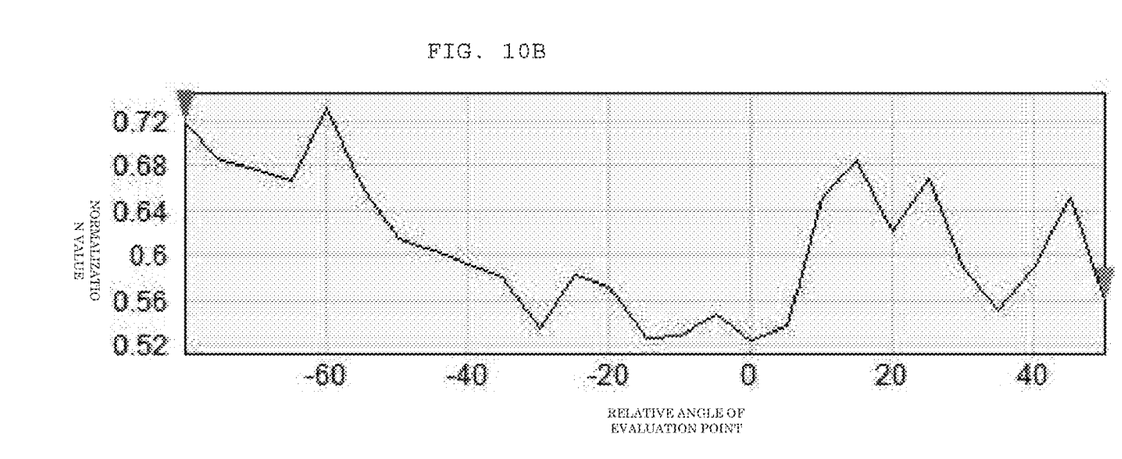
FIG. 10B is a graph illustrating the normalization values of evaluation points in the image of the tooth illustrated in FIG. 9B.

For example, in the example shown in FIG. 9B, 27 evaluation points Peva are set. FIG. 10A is a graph illustrating the luminance of each of evaluation points in the image of the tooth illustrated in FIG. 9B. FIG. 10B is a graph illustrating the normalization value of each of evaluation points in the image of the tooth illustrated in FIG. 9B. After the reference point and the evaluation points are set, the normalization unit 23 normalizes the gray scale values of the evaluation points, and the dental health assessment data generator 24 generates graphs as shown in FIGS. 10A and 10B. As described above, according to the dental health assessment assisting system 100 according to the present embodiment, the imaging apparatus 10 images a fluorescence image of a tooth, and the dental health assessment assisting apparatus 20 analyzes the fluorescence image to generate dental health assessment data, and the display apparatus 30 displays the dental health assessment data. A dentist refers to the dental health assessment data displayed by the display apparatus 30 to comprehensively assess the dental health, for example, whether the tooth is a strong tooth or a weak tooth.

As described above, the embodiment has been described as an example of the technique in the present invention. For this purpose, attached drawings and detailed description are provided.

Thus, the attached drawings and components described in the detailed description can include not only components essential to solve the problems but also components which are not essential to solve the problems but are shown to illustrate the above-described technique. Thus, the components which are not essential should not directly be recognized as essential based on only that they are included in the attached drawings and/or are described in the detailed description.

Moreover, the above-described embodiment illustrates the technique in the present invention, and therefore, various modifications, replacements, addition, omission, and the like can be performed within the scope of the claims or within the scope of the equivalent thereof.

REFERENCE SIGNS LIST

100 Dental Health Assessment Assisting System
10 Imaging Apparatus
20 Dental Health Assessment Assisting Apparatus
21 Gray Scale Converter
22 Gray Scale Value Acquiring Unit
23 Normalization Unit
24 Dental Health Assessment Data Generator
30 Display Device

The invention claimed is:

1. A dental health assessment assisting apparatus comprising:
a gray scale converter configured to convert a fluorescence image obtained by imaging fluorescence of a tooth irradiated with excitation light into a gray scale image;
a gray scale value acquiring unit configured to acquire gray scale values of a reference point and a plurality of evaluation points in an image of the tooth in the gray scale image; and
a dental health assessment data generator configured to generate dental health assessment data visually representing the gray scale value of the reference point and the gray scale values of the plurality of evaluation points; wherein
the gray scale value acquiring unit is configured to extract an entire image of the tooth from the gray scale image to obtain the center of gravity or the center of the entire image of the tooth,
to set, as the reference point, a point having a maximal luminance in the entire image of the tooth, and
to set, as the plurality of evaluation points, points located on a plurality of virtual lines with a predetermined distance from an edge of the tooth in a direction to the center of gravity or the center, the virtual lines passing the center of gravity or the center and forming a predetermined angle with respect to a 0-degree axis connecting the center of gravity or the center to the reference point.

2. The dental health assessment assisting apparatus according to claim 1, wherein
the dental health assessment data generator is configured to generate a graph representing aging of the gray scale value of the reference point and the gray scale values of the plurality of evaluation points as the dental health assessment data.

3. The dental health assessment assisting apparatus according to claim 1, wherein
the reference point is a point at a maximum elevated portion of an occlusion surface of a tooth, and
the evaluation points are points at a marginal portion of the tooth.

4. A dental health assessment assisting system, comprising:
the dental health assessment assisting apparatus according to claim 1, wherein
an imaging apparatus configured to generate a fluorescence image by irradiating a tooth with excitation light to image fluorescence of the tooth, and
a display apparatus configured to display the dental health assessment data generated by the dental health assessment assisting apparatus.

5. The dental health assessment assisting apparatus according to claim 1, further comprising:
a normalization unit configured to normalize the gray scale values of the plurality of evaluation points by the gray scale value of the reference point, wherein
the dental health assessment data generator is configured to visually represent the gray scale values of the plurality of evaluation points normalized by the normalization unit in the dental health assessment data.

6. The dental health assessment assisting apparatus according to claim 5, wherein
the normalization unit is configured to normalize the gray scale values of the plurality of evaluation points by dividing the gray scale values of the plurality of evaluation points by the gray scale value of the reference point.

* * * * *